(12) United States Patent
Fiore

(10) Patent No.: US 6,585,721 B2
(45) Date of Patent: Jul. 1, 2003

(54) CATHETER SHROUD WITH CONDUIT, COLLECTOR AND IMPROVEMENTS

(76) Inventor: John M Fiore, 53 Moonlawn, Troy, NY (US) 12180

(*) Notice: Subject to any disclaimer, the term of this patent is extended or adjusted under 35 U.S.C. 154(b) by 165 days.

(21) Appl. No.: 09/790,387

(22) Filed: Feb. 21, 2001

(65) Prior Publication Data

US 2001/0007060 A1 Jul. 5, 2001

Related U.S. Application Data

(63) Continuation-in-part of application No. 09/307,831, filed on May 10, 1999.

(51) Int. Cl.[7] ............................................. A61M 27/00
(52) U.S. Cl. ...................... 604/544; 604/171; 604/271
(58) Field of Search ................................ 604/121, 519, 604/172, 174, 192, 198, 264, 271, 346, 347, 349, 544, 317, 171; 206/363, 364, 438, 571

(56) References Cited

U.S. PATENT DOCUMENTS

| 3,421,509 A | 1/1969 | Fiore |
|---|---|---|
| 3,894,540 A * | 7/1975 | Bonner, Jr. ................. 604/171 |
| 4,062,363 A | 12/1977 | Bonner, Jr. |
| 4,652,259 A | 3/1987 | O'Neil |
| 5,531,717 A | 7/1996 | Roberto et al. |
| 5,792,114 A | 8/1998 | Fiore |

* cited by examiner

*Primary Examiner*—Manuel Mendez
*Assistant Examiner*—Michael M. Thompson
(74) *Attorney, Agent, or Firm*—Fredric Morelle

(57) ABSTRACT

A flexible, membranous envelope, in a shroud-conduit-collector configuration for sheathing a catheter. In basic mode, the shroud, which essentially envelops the catheter, is partially disposable in an end of the catheter and is extractable therefrom by manipulation of the user. The shroud joins the conduit, that terminates in an integral, yet separable collector. To cure the basic mode's sole limitation, possible infusion of urethra secretions into the opening of the incipiently inserted catheter, a plurality of leaves are attached by their base margins to the shroud exterior, near enough to the inserted opening that their unattached, leading margins can be folded by interleaving them over, and covering, the opening. By this device, an alternate embodiment avoids the catheter-disposed shroud. Other devices are integrated to facilitate manipulation, as well as to aid in after-use separation, sealing and handling of the collector.

15 Claims, 5 Drawing Sheets

CATHETER SHROUD WITH CONDUIT, COLLECTOR AND IMPROVEMENTS

CROSS-REFERENCES TO RELATED APPLICATIONS

This application is a Continuation-in-Part of U.S. application Ser. No. 09/307,831, filed on May 10, 1999 (in issue), priority therefor being claimed under 35 U.S.C. 120.

BACKGROUND OF THE INVENTION

1. Field of the Invention

This invention relates generally to devices that are used in connection with catheters and, specifically, to membranous shrouds or envelopes that are employed to cloak a catheter in order to facilitate sterile (aseptic) insertion of such into a bodily passage. The shroud, or envelope, of the present invention improves that of the earlier art, hereinafter disclosed, by the addition of a shrouding adjunct that lessens the likelihood of urethra contamination. It also includes aids for handling and emptying the collector. The principal distinction of this invention is that it entertains the use of a shorter catheter, in a diminutive shroud-conduit-collector package that may be used for self-catheterization by paraplegics.

2. Discussion of Relevant Art

There exists in the field a need for an apparatus that will allow one limited physically, say by paraplegia, to perform self catheterization and void the bladder, either fully or partially (e.g., taking a specimen sample). Further, the individual performing this auto-procedure should be able to collect a clean specimen, truncate both procedure and apparatus conduction (i.e., fluid flow to a collector) and resume voiding into a portable urinal that is often close to, or part of, the wheelchair apparatus. Although art exists that will allow aseptic or sterile catheterization and uncontaminated fluid collection/containment, and ready disposability of the apparatus, there does not exist the unique combination of elements seen in the instant invention for accomplishing the aforesaid auto-procedure.

Over thirty years ago, I suggested catheterizing a patient with a catheter that was itself prevented from contacting the wall of the urethra, until it had passed into uncontaminated portions of the urethra. To achieve this, an envelope or shroud, i.e., a sterile barrier is interposed the catheter and the urethra wall. The apparatus used consisted in a standard catheter enveloped, at its distal portion, in a tubular membrane (the shroud). A short portion of the shroud is initially passed into the catheter's distal orifice and stored in the catheter. Upon insertion of the catheter distal end into the urethra, with concomitant mechanical or manual retardation of the shroud, the stored shroud is withdrawn from the catheter. This withdrawal of the shroud, as the catheter advances, causes a simultaneous interposition of the shroud between the catheter and wall of the urethra. As may be reckoned, the use of the shroud is no longer novel; however, the instant invention places it to the (self) application mentioned in the Field of the Invention and provides several adjuncts to my basic shroud-conduit-collector combination.

Before discussing the art relevant to my reasons for eclipsing the early shroud usage, I will discuss all the pertinent features of my U.S. Pat. No. 3,421,509 ('509), for an URETHRAL CATHETER. It discloses a catheter which has inserted in its distal end (i.e., with respect to the user, who manipulates the device from its proximal end) a membranous, tubular envelope, which is inserted in and extracted out of the catheter, as its distal end is advanced into the urethra. To facilitate withdrawal of the envelope, an annular sleeve and guard portion or collar, which is attached to a hem of the envelope, is provided to slide over the catheter. As the catheter advances (forward) into the urethra, the sleeve is urged rearward, towards the catheter's proximal end, by manipulation or mechanically by contact against the glans/urethra orifice, and the envelope is extracted. The envelope, or shroud, of this invention does not include an integral container and it is the catheter that provides a conduit to the collection reservoir. This arrangement necessitates use of an introducer element which, like the catheter conduit and collector, is not wholly one piece with the envelope/shroud. Finally, a limitation extant in all shrouded catheters of the present day is likewise present in '509; namely, the tip orifice of the catheter may pick up effluvial contamination within the urethra as it incipiently transits the duct. Quite possibly, the contamination will be carried into the bladder and, most likely, it will be passed into the non-contaminated portions of the urethra. All subsequently discussed art suffers this limitation and, considering my purpose for which the instant invention was made, much more.

Another sheathed catheter is disclosed in U.S. Pat. No. 4,652,259 ('259), entitled CATHETER ASSEMBLY. This disclosure shows a catheter disposed within an outer sheath, the outer sheath composed of two co-linear tubular members. A containment feature, providing a flexible shroud, is in reality a sterile covering that encloses the juncture of the two tubular members. Thus, its function is to maintain sterile conditions within the sheath proper. It is not a container, in the conventional sense, and does not do what is desired by the instant inventor. Also relevant to the instant invention is U.S. Pat. No. 5,531,717 ('717) for NON-CONTAMINATING PROBE AND METHODS OF MAKING AND USING SAME, a sheathed catheter assembly. This patent discloses an annular collar that is attached to a hem of a sheath member and is provided in order to allow the user to manipulate (the extraction of) the sheath. My more recent patent, U.S. Pat. No. 5,792,114 ('114), for INTRODUCER FOR STERILE INSERTION OF CATHETER, also employs a non-integral collar. The envelope (termed "shroud") therein is distinctive over the envelopes or sheaths of the aforementioned patents in that it has only one open end; but, the closed end, although possessing a small cavity, cannot be said to contain an integral fluid receptor/collector. Furthermore, the integrity of this closed-end design is violated by the operational introduction of the catheter.

None of the current art reveals a single-piece shroud-conduit-collector nor, for that matter, a single-piece shroud-collector, that is small enough to be used by the patient him/herself. Moreover, nowhere in the art is there disclosed a one-piece apparatus for the aseptic enshroudment of a catheter, conduction of body fluids to, and a reservoir for, those fluids. Finally, it can be seen that even shrouded catheters do not avoid the aforementioned limitation of '509, entry of contamination into the shrouded catheter tip.

INCORPORATION BY REFERENCE

Because of their relevance to certain features of the instant invention, as well as their provision of background art and terminology, the following previously discussed U.S. patents are hereinafter incorporated by reference: U.S. Pat. No. 3,421,509, entire disclosure; U.S. Pat. No. 4,652,259, column 2 and FIGS. 1 and 6; U.S. Pat. No. 5,531,717, FIGS. 2–9, 12, 13 and columns 1 and 2; and U.S. Pat. No. 5,792,114, entire disclosure.

DEFINITIONS

Most terms are defined parenthetically herein or may be determined by context and by referring to the drawings of both incorporated references and the instant art. A few terms and their synonyms or analogs are defined:

"aseptic" is used synonymously with "sterile";

"bulbous" means expansive and does not connote a particular form or shape;

"collar" means an encircling or girdling element or surface relief; such an element in the present invention, a relieved surface, serves as a manipulative device;

"envelope" means the flexible, membranous subject of the invention, also the words "sheath" or "shroud";

"integral with/to" means within the unit in the forming or making of an object;

"monolithic" has the meaning given it in the BRIEF SUMMARY OF THE INVENTION;

"one-piece" means a single continuous unit, whether formed monolithically or formed, molded or cast in separate sections that are joined subsequently by suitable means;

"proximal" refers to a device's portion that is inserted into the body, i.e., in this invention, closer(est) to the human body (urethra) being catheterized;

"singular piece" means the same as "one-piece"; and

"wholly" or "unitary" mean the same as "one-piece" or "singular piece".

BRIEF SUMMARY OF THE INVENTION

The basic device on which the herein disclosed improvements are made consists in a singular piece of fluid-impervious, membranous envelope that may be continuously formed, of a single substance, to provide a catheter shroud- (or sheath-) fluid conduit-collector. The latter is a concatenated, short-necked reservoir. Alternately, the invention consists in a singular piece realized by a continuous structure wherein the three distinct portions thereof are physically joined, one to the other(s), by any of the contemporary manufacturing processes such as adhesion, cohesion or welding. In keeping with a standard adopted in the Patent Office, I refer to the first, continuously formed article, as "monolithic" and the second, continually or piecemeal formed, simply as "integral" or "unitary". Neither of these two embodiments are seen in the art; and, also novel is the likely usage of a short catheter (about 10–12 cm.) that is, when used properly, one which may be preponderantly disposed in the urethra, with but 2–5 cm. anticipated to remain outside, to facilitate finger-tip withdrawal. In its normal, ready-to-use configuration, the catheter is enshrouded by the shroud portion and part of the fluid conduit portion, the latter portion being storable on the rear part of the catheter, as an aid in packaging. Should it suit the manufacturer, for ease of sterilization and compactness in packaging, the entire conduit and collector may also be placed onto the catheter; however, this is a storage, rather than an operative mode. In operation, the catheter does not join the collector. This is most important because integrity of the conduit-collector section is violable and, after it is filled with fluid, the collector is readily separable from the conduit portion, unhindered by the catheter. This is done with little physical effort by the paraplegic user, because the catheter device is itself not integrated with the collector. As reference to this disclosure's priority document will show, a portion of the shroud is initially disposed in the proximal end of the catheter and is withdrawn as the latter is pressed into the urethra. As it leaves the catheter proximal end, the shroud is interposed the catheter and the urethra wall, its primary purpose being to provide a sterile path for the catheter as it transits the urethra into the bladder. To statically maintain the conduit during catheter insertion, as well as separation and closure of the collector from the ensemble proper, suitable adjuncts are provided such as a distal surface relief on the shroud exterior, a rending facility and a tongue-in-groove closure, respectively.

Differing from the above described and original, "basic" device are the shroud and adjuncts of the instant invention. First and foremost, the shroud, which is disposed in the catheter proximal end, bears near that end, a plurality of tabs or leaves that are attached by their distal margins to the circumference of the shroud exterior. The leaves are stylistically folded (overlapping or interleaving) over the shroud-enveloped proximal end of the catheter. This interleaving of integral shroud portions (hereinafter, "leaves") operatively effects a continuous sheathing of the catheter as it is initially pressed into the urethra, thus avoiding possible infusion of urethra secretions into the proximal opening of the incipiently inserted (and shrouded) catheter. Thereafter, the shroud portion's distal end is maintained static by the user's fingertips and the catheter is advanced further into the urethra and into the bladder. The rending and closure adjuncts, mentioned above, are maintained; and, additionally a handle and an evacuation device are added to the collector portion.

The evacuation device is a mechanism that is positioned at most any place on the collector to facilitate emptying of the reservoir. It consists, primarily, of a flanged annular guide or jig, fixed to the collector surface and a flanged annular chisel, positioned in the guide and held off the surface by a cushion interposed between the flanges. Pressing the chisel toward, and compressing, the cushion effects a piercing of a seal or the collector surface.

DETAILED DESCRIPTION OF THE INVENTION

A great deal of effort is expended today in order to assure that persons having physical disabilities are afforded appliances and facilities that will inure to their comfort and well-being. In a small, but significant way, the instant invention supplements that effort, while concomitantly insuring sterility, and thus safety, when using a urinary catheter. As disclosed above, I have provided this invention to my shroud-conduit-collector ensemble; however, the interleaving "shield" is, in fact, an extendable shroud that is readily adaptable for use with any catheter, to preclude entry into the catheter tip of contaminant or foreign matter that may be present in the urethra. Thus, it is an improvement to my basic shroud-conduit-collector invention and a novel device in and of itself.

Figure 1:
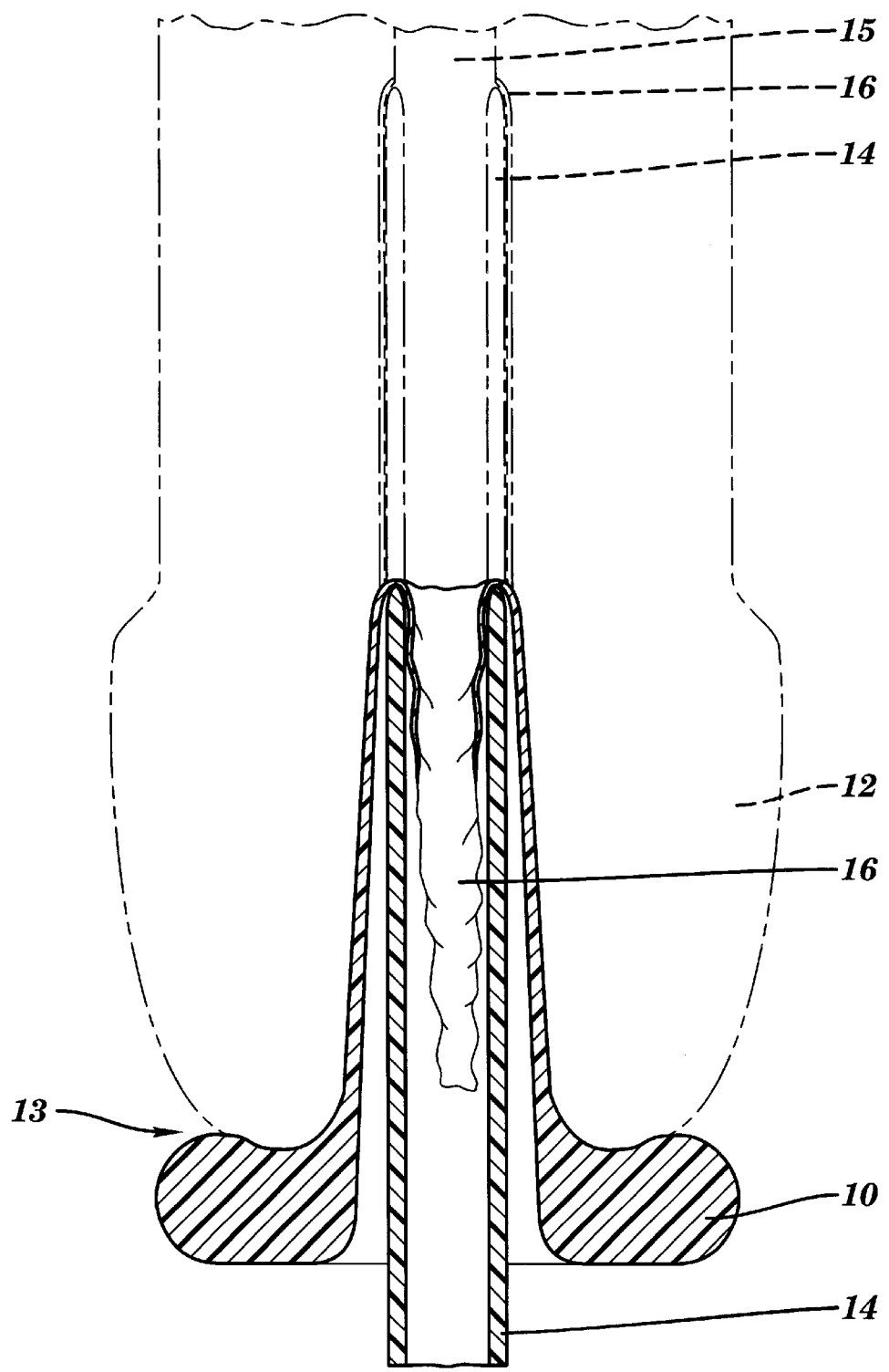
FIG. 1 is a prior art illustration of catheter-stored shroud and introducer.

Referring to FIG. 1, there is illustrated, in part and as prior art, my invention of patent '509. The principal feature is an introducer 10 that is pressed into the urethra 15, at the glans penis 12. Unitary with the introducer is a membranous tube 16, subsequently termed "shroud", that is attached at its hem about the tip of the introducer and inserted into the separate catheter 14. As the catheter is urged through the static introducer (its static posture, assured by the retardant effect of the glans against the introducer-collar 13), the tubular membrane is withdrawn and interposed between the catheter and the urethra wall (Cf. in phantom, items 14 and 16).

Figure 2:
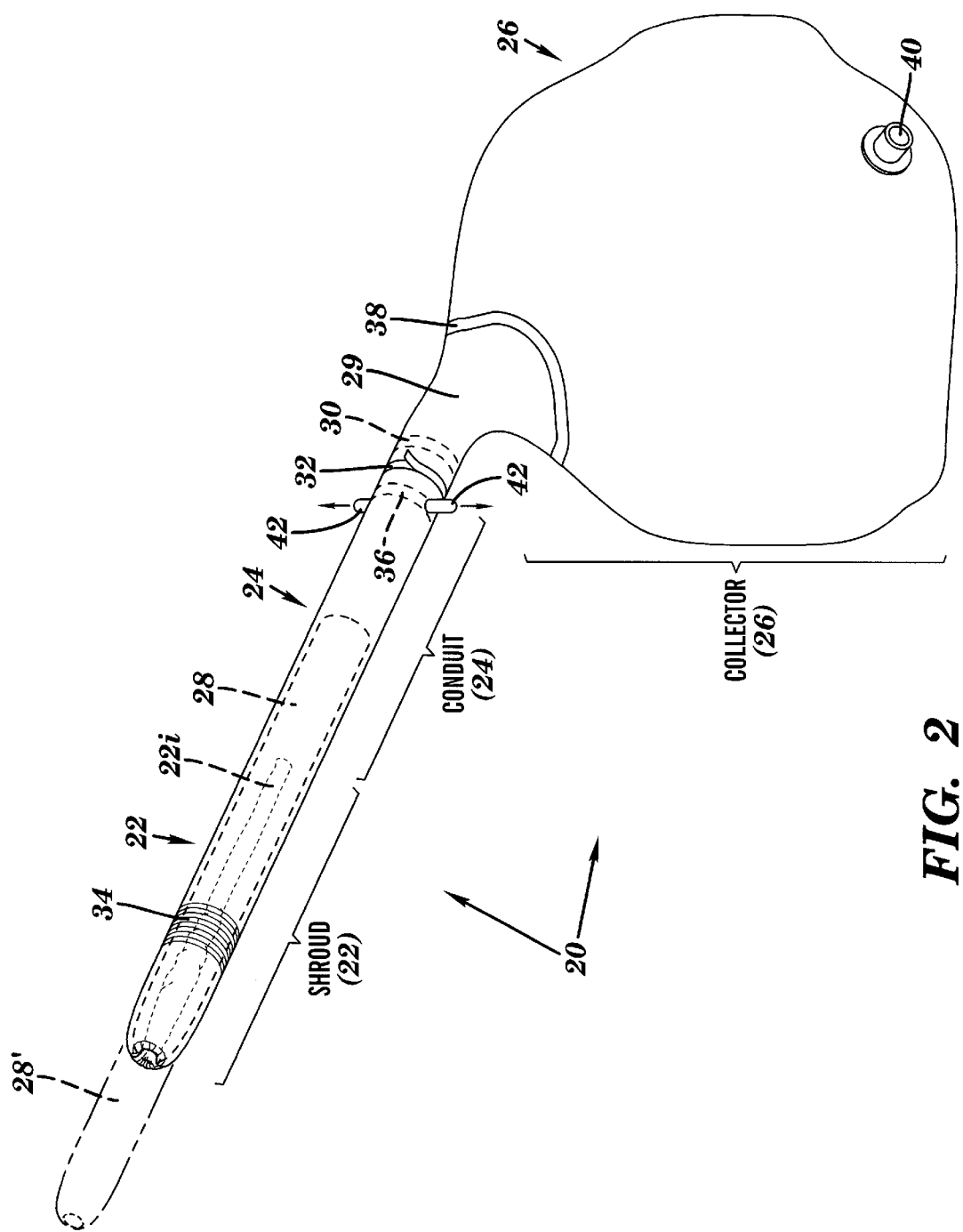
FIG. 2 is an illustration of the basic shroud-conduit-collector of the invention with later adjuncts disclosed.

FIG. 2 presents the features of the basic invention 20 consisting of three portions: a shroud 22, a conduit 24 and a collector 26. The shroud portion is shown enveloping a catheter 28 in its inactive mode, that is, nested in the proximal end of the (basic) shroud-conduit-collector unit 20. In phantom, a part of the shroud is shown inserted into the catheter 22i. As the catheter is advanced (28') into the urethra, the shroud is withdrawn from within and interposed between the urethra wall and the catheter (more expressly drawn in FIG. 3).

The other elements of FIG. 2 are present in the basic invention: a tongue-and-groove mechanism 30, located internally of the short collector neck 29 and used to seal the collector after a desired amount of urine is voided; a separation device, to sever the collector from the conduit 24; and, an area of surface relief 34, to aid in maintaining the shroud static during insertion of the catheter (note the absence of an introducer-collar). After initially pressing the tip of the catheter into the urethra orifice, the user generally places a finger at the distal end of the shroud-covered catheter and advances it into the urethra while concurrently grasping the surface relief 34 to keep the distal end of the shroud relatively static. This action emulates the use of the (introducer) collar of the prior art. Three adjuncts are added to the unit 20 as part of the instant invention. They are: a second tongue-and-groove seal 36; a handle 38, on the collector; and, an evacuation port 40. The latter is discussed more fully at FIGS. 8 and 9.

The reader should note that the catheter 28 used herein is not the usual elongated tube, but rather, is unconventionally short. The catheter is not connected to the collector and thus does not impede severance of the collector from the ensemble, or unit 20, by pulling tear strip 32. However, even having been invented for the person having no bladder control, the basic invention 20 did not contemplate the user drawing less urine than the bladder held. Thus, it is necessary to supplement it with a second seal to close off the conduit, allowing urination to be temporarily curtailed and the (sealed) collector to be severed from the conduit. Once detached, the (tear strip 32-severed) collector is then moved by means of the handle 38 (literally, it becomes liquid-filled balloon) to a safe repository and the user, freed of the collection burden, may continue voiding into the urinal. In order to continue, the second seal 36 must be opened; and, this is done by grasping external tabs 42, and tugging lightly to open the seal.

Figure 3:
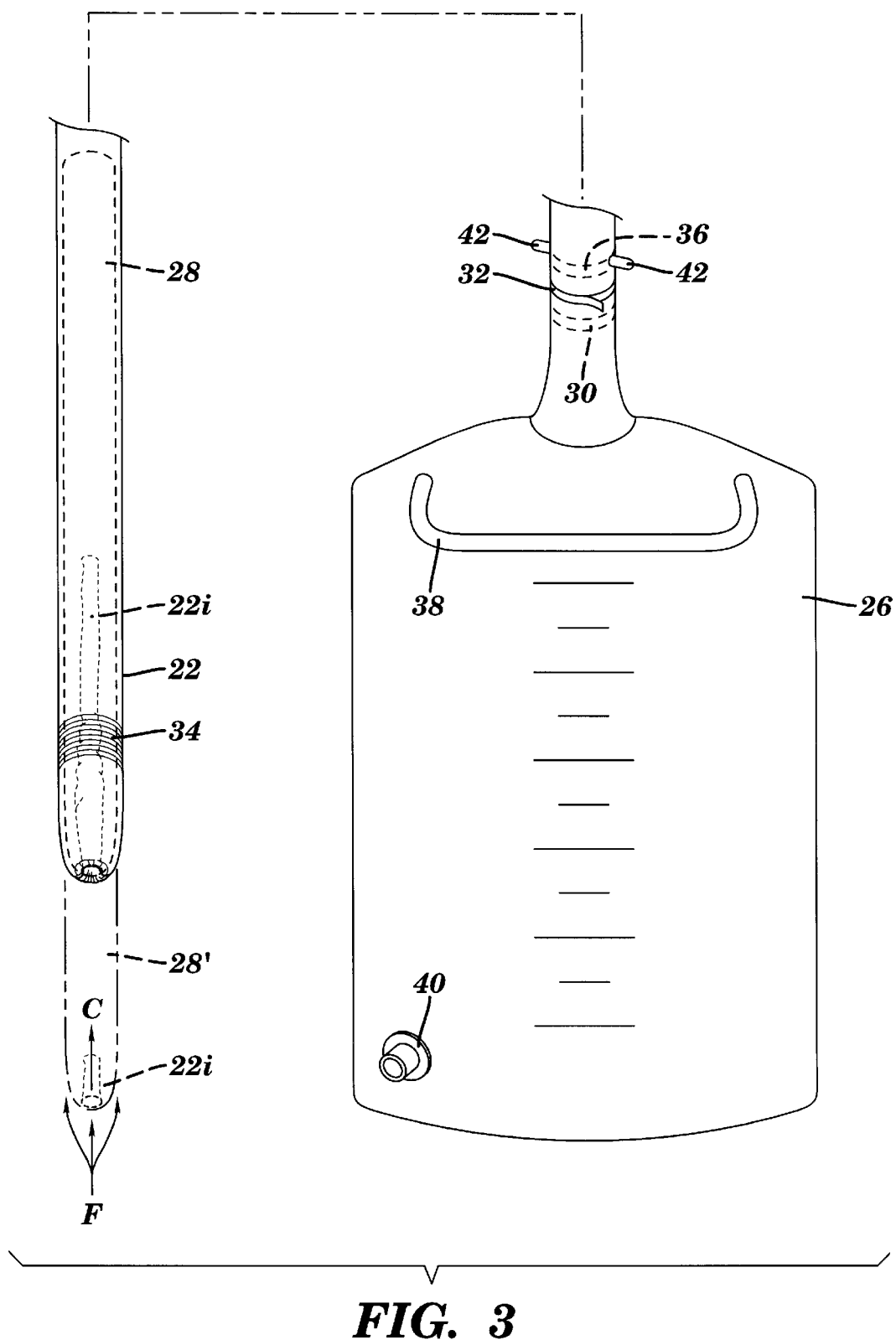
FIG. 3 is an illustration of the FIG. 2 device in alternate shape.

The FIG. 3 illustration shows essentially the same device as seen in FIG. 2, but in a style or mode of manufacture representative of piecemeal, rather than monolithic (single-piece), construction. All integral parts being the same, the reader's attention is drawn to the image of the prospectively (in phantom) advanced catheter 28'. There, one sees the inserted shroud 22i practically withdrawn and the basic invention's 20 sole limitation, infusion of urethra contaminants into the interior of catheter 28', defined by a small portion C of the effluent F. It is the prevention of this possible event to which the instant invention of this disclosure is directed.

Figure 4:
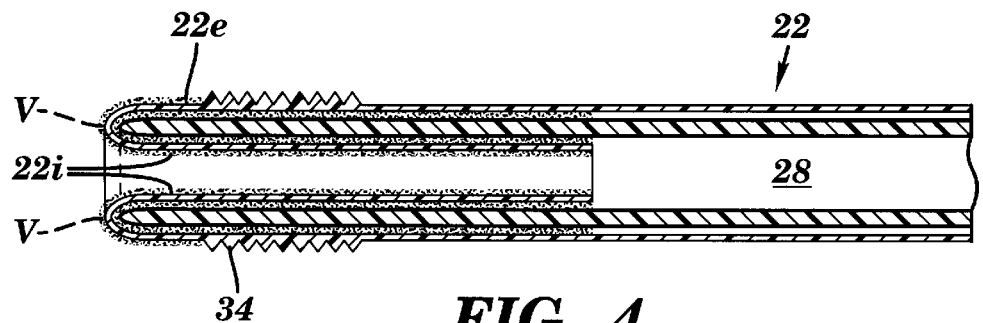
FIG. 4 is a cross section of the catheter proximal end with the shroud nested therein.

Referring to FIG. 4, the proximal end of the catheter 28 is sheathed by shroud 22 consisting of two sections, the first 22i which is inserted into the shroud, and the second or exterior 22e. Since the shroud is a membranous continuum, these sections are only virtually separated, i.e., by a virtual boundary V, located adjacent to the relieved surface 34, as shown. This arrangement is that of the basic invention shown in FIG. 2.

Figure 5:
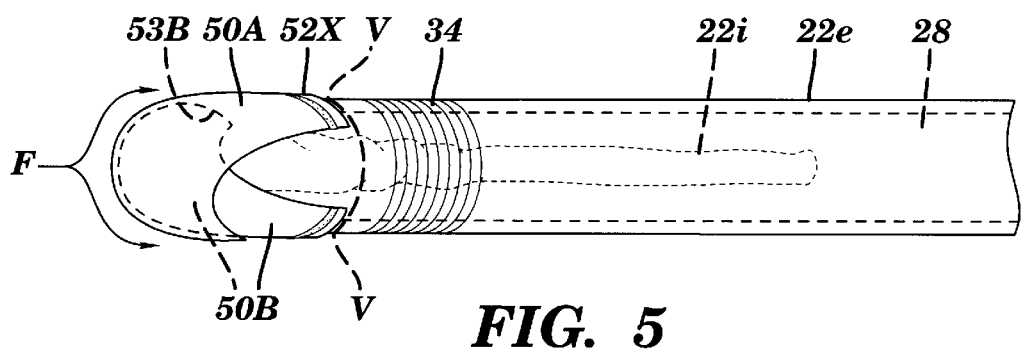
FIG. 5 is a drawing of the present invention.
Figure 6:
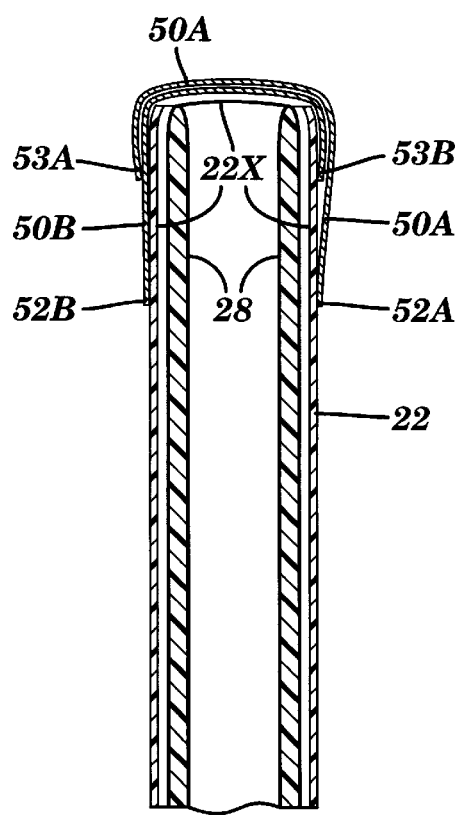
FIG. 6 is a cross section of the present invention absent a catheter-inserted shroud portion.
Figure 7:
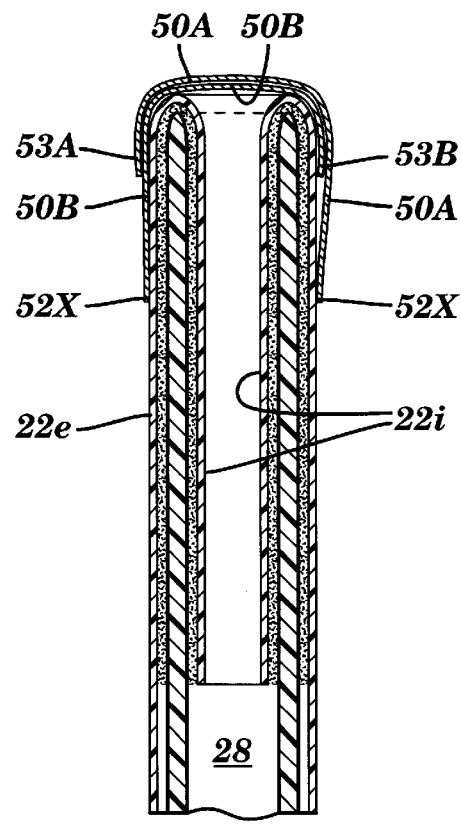
FIG. 7 is the FIG. 6 device bearing a catheter-disposed portion of the shroud.

The instant invention is shown in FIGS. 5, 6 and 7. Of these drawings, FIG. 6 shows the improvement completely independent of the basic invention, that illustrated in FIGS. 5 and 7. Having reference first to FIG. 5, the device of FIG. 4 is presented completely, in isometric detail. The improvements, at least two leaves 50A, 50B are attached by their distal margins to the shroud exterior, proximate the boundary V. Here, only two leaves, partially covering the catheter tip area, are shown for the sake of clarity. Since their purpose is to shield the interior of the catheter from intrusion by contaminants F, they are placed in an interleaved or overlapping arrangement; here, leaf 50B is drawn at least over the catheter's open end and, preferably, down a portion of the side opposite its attached margin 52X. Remaining leaves, such as 50A are arranged, et seq., overlapping 50B, etc. Sterile lubricant (not shown) is disposed between the leaves, between them and the shroud and between shroud and catheter to effect frictionless movement between all these parts. As the device is inserted into the urethra, the shroud being maintained relatively static, shroud section 22i is withdrawn and the leaves begin to slide apart; the contaminant fluid F is directed about the device, as shown, and captured between the relatively static shroud exterior 22e and the urethra wall (not shown). By this action, the leaves are withdrawn from over the catheter opening as the tip passes into the uncontaminated portion of the urethra (see references). A view of this arrangement is seen in cross section at FIG. 7. For the sake of clarity, the contaminant F, the shroud sectional boundary V and the relieved surface 34 are not shown. This view also displays to the reader how, absent the instant improvement, contaminants can enter the catheter, or at least surfaces of the exiting shroud, and be deposited into the uncontaminated urethra or bladder.

An alternate embodiment, more functional and easier to manufacture than that of the previously discussed figures, is shown in FIG. 6. This embodiment shows the leaves 50A/B,53A/B disposed over and down the sides of the catheter 28. However, the shroud portion 22i is deleted. Whereas the FIGS. 5/7 configuration only required a minimal leaf length (enough for the tip to reach the uncontaminated urethra), the FIG. 6 embodiment requires this and possibly a third leaf to assure non-entry of the slightest amount of contaminant. The advantage of the alternate embodiment is that the shroud need not be as lengthy; in fact, the shroud part in FIG. 6, denoted as excess 22X, may be readily truncated and the leaves 50A, et seq., made confluent to the shroud part 22e. This is done by distending the shroud (in much the same manner as can be done with the collector), but mechanically bifurcating, trifurcating etc. the insertable section 22i, to effect the desired multiplicity of leaves. Thus, the shown leaf welds or attachments 52A/B are avoided and a truly singular-piece device is realized.

Figure 8:
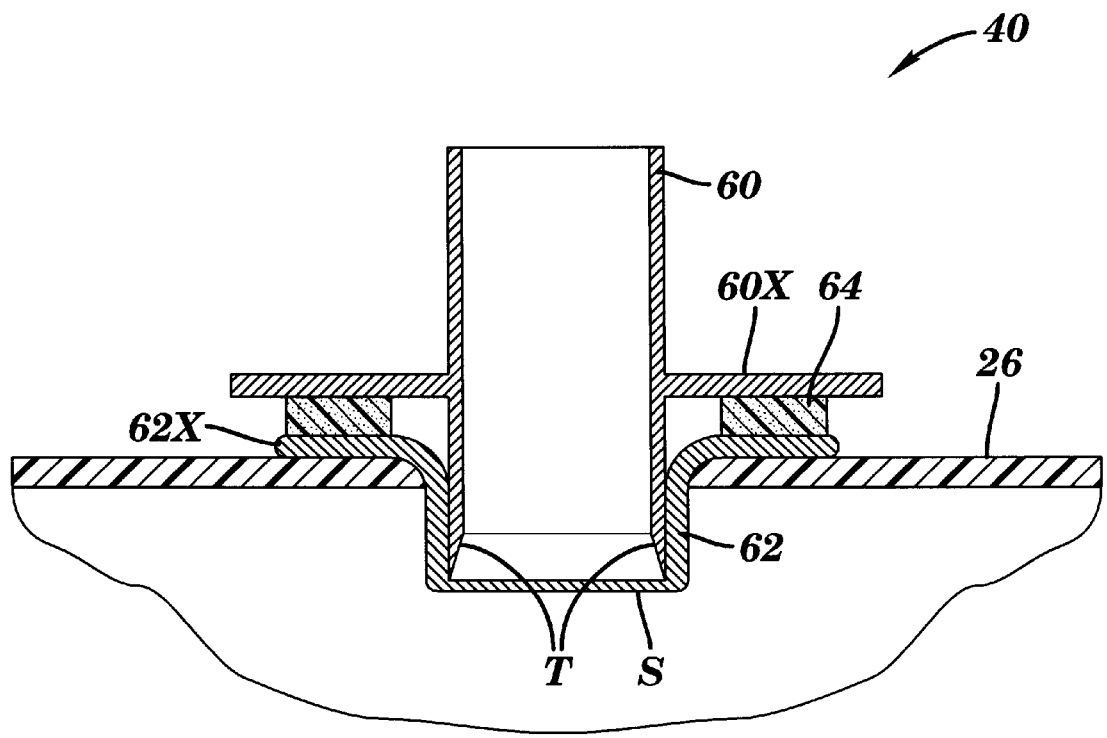
FIG. 8 is a cross sectional elevation of the evacuation port, inactivated.
Figure 9:
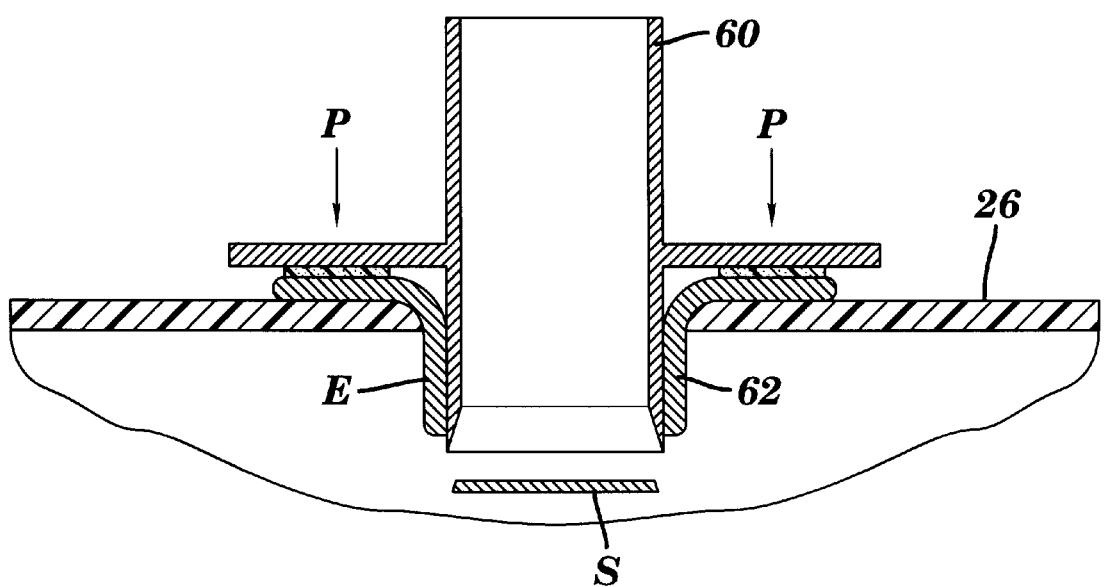
FIG. 9 is a cross sectional elevation of the evacuation port, activated.

Emptying of the filled collector 26 is effected by actuation of the FIGS. 8 and 9 mechanism. FIG. 8 shows a tubular chisel or needle tool 60 movably set in an annular jig 62. A ring 64 of firm, but compressible material, such as a rubbery latex, is fixedly disposed between, on and to flanges 60X and 62X, that radiate respectively from both the tool 60 and the jig 62. Covering the lower end of the jig is a seal S and, poised above the seal is the sharpened edge T of the tool. When pressure is applied to the top of the tool or its flange 60X, as shown by arrows P in FIG. 9, the seal is ruptured and fluid readily escapes the collector. Alternately, the seal may be realized by constructing the tool-jig assembly with a shorter tubular extension E and affixing it directly to the surface of the collector. Actuation of the mechanism will then pierce the collector directly, resulting in the desired effect.

What is claimed is:

1. A device for enveloping a catheter, said catheter having a proximal open end adapted for insertion into a urethra and a distal open end from which body fluids exit, said device comprising:

a tubular, flexible membrane being a serial concatenation of a catheter-enveloping shroud section a conduit section and a collector section, the shroud section defining a first tubular portion sharing a virtual transverse boundary with a second portion, the first portion of the shroud section;

an urethral catheter;

at least two membranous leaves each having proximal and distal ends, said distal ends being circumferentially attached to an external surface of the shroud section, on its second portion and sufficiently distant from the transverse boundary to allow said leaves to be folded in an interleaved fashion over the catheter proximal open end.

2. The device of claim 1 wherein the conduit section comprises a flow path for said body fluids to the collector section and has at a distal part thereof a rending tear strip for severing the collector section therefrom.

3. The device of claim 2 further comprising at least a pair of sealing means for closing off said flow path, each one of said pair disposed adjacent to and straddling said rending strip.

4. The device of claim 1 further comprising a handle fixed at a proximal region of the collector section.

5. The device of claim 1 also having a membrane-piercing sharp tool, disposed at a distal region of the collector section.

6. A device for enveloping a catheter, said catheter having a proximal open end adapted for insertion into a urethra and a distal open end from which body fluids exit, said device comprising:

a tubular, flexible membranous shroud having a first portion mid a second portion, the catheter receptive of the first portion of the shroud into its proximal end;

at least two membranous leaves having proximal and distal ends, said distal ends each being integral with an external surface of the shroud, on the second portion, sufficiently distant from a virtual transverse boundary between the first and second portions to allow said leaves to be folded in an interleaved fashion over the catheter proximal open end.

7. The device of claim 6 further comprising a conduit means and a collector means concatenated serially to and integral with the shroud, said collector means bearing thereon a handle and a membrane-piercing chisel-type tool.

8. A device for substantially enveloping a catheter that has a proximal open end adapted for insertion into a urethra and a distal open end from which body fluids exit, said device comprising:

a flexible, membranous shroud having a first proximal portion and a second distal tubular portion;

said first proximal portion comprising at least two membranous leaves having proximal and distal ends, said distal ends each being circumferentially confluent with the second distal portion and adapted for interleaved folding over the catheter proximal open end.

9. The device of claim 8, further comprising a conduit means, for conveying said fluids, and a container, for collecting said fluids, the conduit means and container being concatenated serially with the shroud.

10. The device of claim 9 wherein said conduit means comprises a tubular, flexible fluid conduit concatenated with the shroud and said container is a fluid collector that is integrally concatenated with the conduit.

11. The device of claim 10 wherein the conduit comprises a flow path for said body fluids to the container and has at a distal part thereof a rending strip for severing the container from the conduit.

12. The device of claim 11 further comprising at least a pair of sealing means for closing off said flow path, each one of said pair disposed adjacent to and straddling said rending strip a first member of said pair disposed between the strip and the conduit.

13. The device of claim 9 further comprising a handle fixed at a proximal region of the container.

14. The device of claim 9 also having a membrane piercing chisel, disposed at a distal region of the container.

15. The device of claim 12 further comprising diametrically opposing tabs, said labs fixed to an outer surface of the conduit and over the first member of said pair of sealing means.

* * * * *